United States Patent
Tahmasian et al.

(10) Patent No.: US 8,983,615 B2
(45) Date of Patent: Mar. 17, 2015

(54) SYSTEM FOR COMMUNICATION WITH IMPLANTABLE MEDICAL DEVICES USING A BRIDGE DEVICE

(75) Inventors: Samuel Tahmasian, Burbank, CA (US); Daniel Ahassian, Glendale, CA (US); Douglas Michael Ackermann, San Francisco, CA (US); Joonho Hyun, Valencia, CA (US); Dennis Ralph Zottola, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/372,177

(22) Filed: Feb. 13, 2012

(65) Prior Publication Data

US 2012/0215285 A1 Aug. 23, 2012

Related U.S. Application Data

(60) Provisional application No. 61/444,842, filed on Feb. 21, 2011.

(51) Int. Cl.
*A61N 1/00* (2006.01)
*H04B 5/00* (2006.01)
(Continued)

(52) U.S. Cl.
CPC .......... *H04B 5/0031* (2013.01); *A61N 1/37217* (2013.01); *A61N 1/37247* (2013.01);
(Continued)

(58) Field of Classification Search
CPC .................................................. A61N 1/3605
USPC .......................................................... 607/59
See application file for complete search history.

(56) References Cited

U.S. PATENT DOCUMENTS 5,548,271 A * 8/1996 Tsuchiyama et al. ........ 340/7.61
5,720,770 A   2/1998 Nappholz et al.
(Continued)

FOREIGN PATENT DOCUMENTS

WO   03095024      11/2003 ............. A61N 1/372
WO   03095024 A2   11/2003

OTHER PUBLICATIONS

International Search report dated May 11, 2012 for Application No. PCT/US2012/025345.
(Continued)

*Primary Examiner* — Christopher D Koharski
*Assistant Examiner* — Nadia Ahmad
(74) *Attorney, Agent, or Firm* — Lewis & Reese, PLLC (57) ABSTRACT

A communications bridge device communicates between a consumer electronics device, such as a smart telephone, and an implantable medical device. The bridge forwards instructions and data between the consumer electronics device and the implantable medical device. The bridge contains a first transceiver that operates according to a communication protocol operating in the consumer electronics device (such as Bluetooth®), and second transceiver that operates according to a communications technique operating in the implantable medical device (e.g., Frequency Shift Keying). A software application is installed on the consumer electronics device, which provides a user interface for controlling and reading the implantable medical device. The software application is downloadable using standard cellular means. The bridge is preferably small, and easily and discreetly carried by the implantable medical device patient. The bridge is preferably also simple to operate, and may have only a simple user interface, or no user interface at all.

34 Claims, 10 Drawing Sheets

(51) Int. Cl.
*A61N 1/372* (2006.01)
*H04W 4/00* (2009.01)

(52) U.S. Cl.
CPC ........ *A61N1/37264* (2013.01); *A61N 1/37282* (2013.01); *H04B 5/0037* (2013.01); *H04B 5/0075* (2013.01); *H04W 4/008* (2013.01)
USPC .......................................................... 607/59

(56) References Cited

U.S. PATENT DOCUMENTS

| | | | |
|---|---|---|---|
| 5,759,199 A * | 6/1998 | Snell et al. | 607/60 |
| 6,219,580 B1 | 4/2001 | Faltys et al. | |
| 6,250,309 B1 | 6/2001 | Krichen et al. | |
| 6,434,429 B1 | 8/2002 | Kraus et al. | |
| 6,442,432 B2 | 8/2002 | Lee | |
| 6,490,487 B1 | 12/2002 | Kraus et al. | |
| 6,497,655 B1 | 12/2002 | Linberg et al. | |
| 6,516,227 B1 | 2/2003 | Meadows et al. | |
| 6,553,262 B1 | 4/2003 | Lang et al. | |
| 6,574,509 B1 | 6/2003 | Kraus et al. | |
| 6,662,052 B1 * | 12/2003 | Sarwal et al. | 607/59 |
| 6,738,671 B2 | 5/2004 | Christophersom et al. | |
| 7,043,305 B2 | 5/2006 | Kenknight et al. | |
| 7,060,030 B2 | 6/2006 | Von Arx et al. | |
| 7,177,698 B2 | 2/2007 | Klosterman et al. | |
| 7,191,012 B2 | 3/2007 | Boveja et al. | |
| 7,313,529 B2 | 12/2007 | Thompson | |
| 7,369,897 B2 * | 5/2008 | Boveja et al. | 607/60 |
| 7,475,245 B1 * | 1/2009 | Healy et al. | 713/168 |
| 7,597,643 B2 | 10/2009 | Shimada | |
| 7,742,821 B1 | 6/2010 | Vamos et al. | |
| 7,848,819 B2 | 12/2010 | Goetz et al. | |
| 7,865,242 B2 | 1/2011 | Diebold et al. | |
| 7,885,712 B2 | 2/2011 | Goetz et al. | |
| 7,978,062 B2 | 7/2011 | LaLonde et al. | |
| 8,002,700 B2 | 8/2011 | Ferek-Petric et al. | |
| 8,103,346 B2 | 1/2012 | Mass et al. | |
| 8,130,093 B2 | 3/2012 | Mazar et al. | |
| 8,140,160 B2 | 3/2012 | Pless et al. | |
| 8,174,395 B2 | 5/2012 | Samuelsson et al. | |
| 8,265,757 B2 | 9/2012 | Mass et al. | |
| 8,373,556 B2 | 2/2013 | LaLonde et al. | |
| 8,395,498 B2 | 3/2013 | Gaskill et al. | |
| 8,410,940 B2 | 4/2013 | Samuelsson et al. | |
| 2004/0088374 A1 | 5/2004 | Webb et al. | |
| 2006/0212092 A1 * | 9/2006 | Pless et al. | 607/45 |
| 2008/0114416 A1 | 5/2008 | Theriot et al. | |
| 2008/0208292 A1 | 8/2008 | Persen et al. | |
| 2009/0024179 A1 | 1/2009 | Dronov | |
| 2009/0063187 A1 | 3/2009 | Johnson et al. | |
| 2009/0112291 A1 | 4/2009 | Wahlstrand | |
| 2009/0210798 A1 | 8/2009 | Wu et al. | |
| 2009/0292340 A1 | 11/2009 | Mass | 607/60 |
| 2010/0229324 A1 | 9/2010 | Conrad | |
| 2010/0305663 A1 | 12/2010 | Aghassian | |
| 2010/0318159 A1 | 12/2010 | Aghassian et al. | |
| 2011/0071597 A1 | 3/2011 | Aghassian | |
| 2011/0112611 A1 | 5/2011 | Aghassian | |
| 2013/0007210 A1 | 1/2013 | Mass et al. | |
| 2013/0073005 A1 | 3/2013 | Aghassian | |
| 2013/0076535 A1 | 3/2013 | Sievert et al. | |

OTHER PUBLICATIONS

Kothandaraman, Sridhar, "Replaceable RF Communications Card for Implantable Medical Device Programmers", Prior Art Database Technical Disclosure, pp. 1-4 (Jul. 3, 2003).
Office Action received regarding corresponding Japanese Patent Application No. JP2013-555453, dated Aug. 11, 2014.

* cited by examiner

SYSTEM FOR COMMUNICATION WITH IMPLANTABLE MEDICAL DEVICES USING A BRIDGE DEVICE

CROSS REFERENCE TO RELATED APPLICATIONS

This Application claims priority to U.S. Provisional Application Ser. No. 61/444,842 entitled "System for Communicating with Implantable Medical Devices Using a Bridge Device" filed Feb. 21, 2011 and which is incorporated by reference in its entirety herein.

TECHNICAL FIELD

The present invention relates to the field of implantable medical devices, and in particular to remote control of implantable medical devices by generic consumer electronic devices.

BACKGROUND ART

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIG. 1, an SCS system typically includes an Implantable Pulse Generator (IPG) 100, which includes a biocompatible case 130 formed of titanium, for example. The case 130 typically holds the circuitry and power source or battery necessary for the IPG 100 to function, although IPGs can also be powered via an external RF energy source and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are 16 electrodes on lead 102, labeled E1-E16, and sixteen electrodes on lead 104, labeled E17-E32, although the number of leads and electrodes is application specific and therefore can vary.

Patients with implanted neurostimulators must have a means for communicating with and controlling their implant. Typically, different stimulation settings are needed to provide complete pain coverage throughout the day. The patient uses an external (remote) controller to adjust the stimulator output to obtain the best therapy. Different therapy settings may be required when the patient is sleeping, standing, sitting, or driving. Some settings may be saved as programs and may be selected by the patient using the external controller. Common uses of the external controller are to increase or decrease the strength of stimulation, to select different areas of the body to be stimulated, and to shut off and turn on stimulation.

Figure 2:
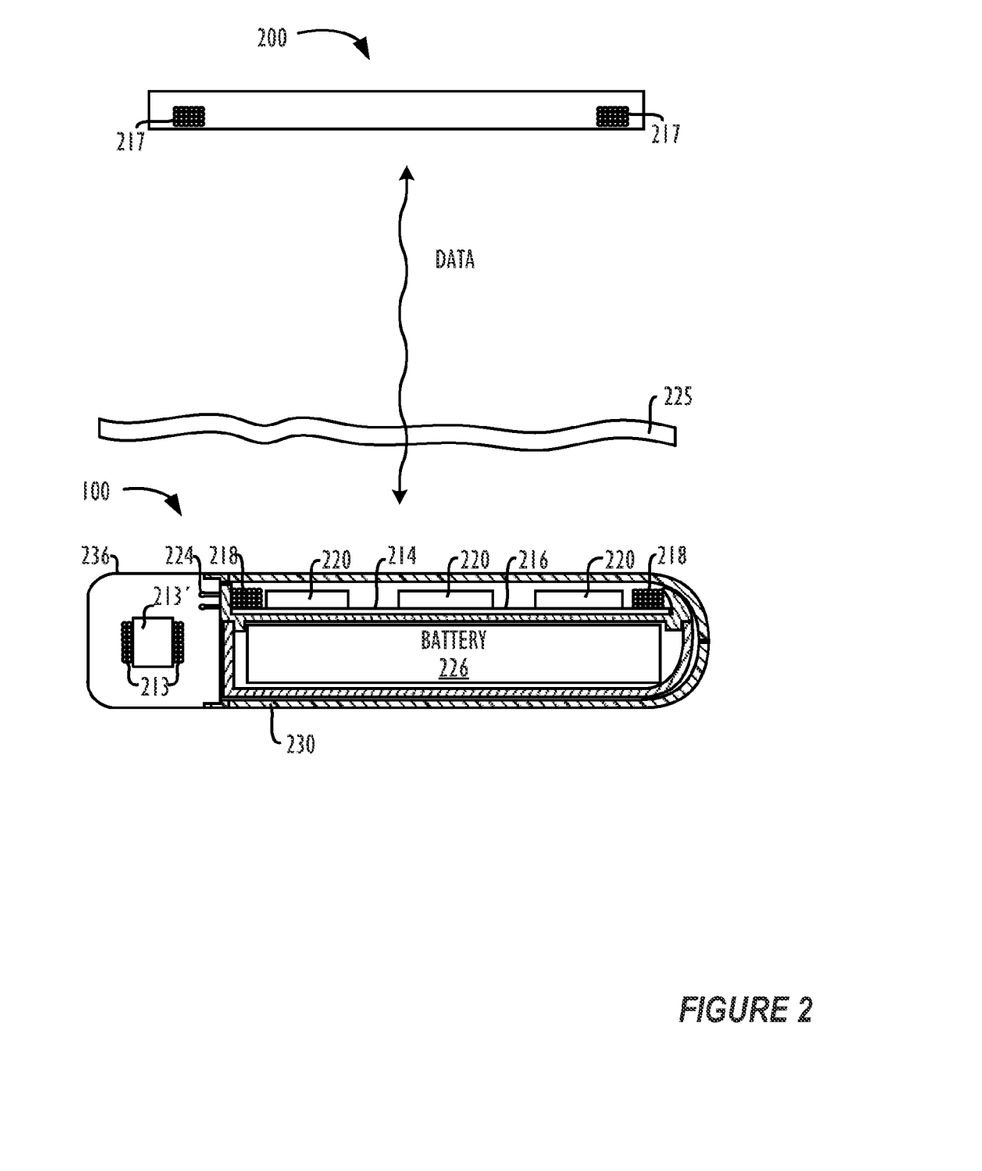
FIG. 2 illustrates the use of an external controller to communicate with an implantable medical device according to the prior art.

FIG. 2 shows portions of an IPG system in cross section, including the IPG 100 and an external controller 200. The IPG 100 typically includes an electronic substrate assembly 214 including a printed circuit board (PCB) 216, along with various electronic components 220, such as a microcontroller, integrated circuits, and capacitors mounted to the PCB 216. Two coils are generally present in the IPG 100: a telemetry coil 213 used to transmit/receive data to/from the external controller 200, and a charging coil 218 for charging or recharging the IPG's power source or battery 226 using an external charger (not shown). The telemetry coil 213 can be mounted within the header connector 236 as shown.

As just noted, an external controller 200, typically a handheld device, is used to wirelessly send data to and receive data from the IPG 100. For example, the external controller 200 can send programming data to the IPG 100 to set the therapy the IPG 100 will provide to the patient. In addition, the external controller 200 can act as a receiver of data from the IPG 100, receiving various data reporting on the IPG's status.

The communication of data to and from the external controller 200 occurs via magnetic inductive coupling. When data is to be sent from the external controller 200 to the IPG 100 for example, coil 217 is energized with an alternating current (AC). Such energizing of the coil 217 to transfer data can occur using a Frequency Shift Keying (FSK) communication technique for example, such as disclosed in U.S. Patent Publication 2009/0024179. Energizing the coil 217 generates a magnetic field, which in turn induces a current in the IPG's telemetry coil 213, which current can then be demodulated to recover the original data. Such inductive communications occur transcutaneously, i.e., through the patient's tissue 225, making it particularly useful in a medical implantable device system.

External controllers 200 available today are developed by medical device manufacturers, and such development requires substantial investments. For one, care has to be taken by the developer to create a user interface for the external controller 200 that patients and clinicians will like and find easy to use. As such, external controllers 200 are typically designed with user interfaces having displays, buttons, speakers, etc. Development of such a user interface is expensive for the medical device manufacturer, and is not easy to change once displayed.

DESCRIPTION OF EMBODIMENTS

The description that follows relates to use of the invention within a spinal cord stimulation (SCS) system. However, the invention is not so limited. Rather, the invention may be used with any type of implantable medical device system that could benefit from improved communication with an implanted device. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

A communications bridge device communicates between a consumer electronics device, such as a smart telephone, and an implantable medical device. The bridge forwards instructions and data between the consumer electronics device and the implantable medical device. To do so, the bridge contains two transceivers: one that operates according to a communication protocol operating in the consumer electronics device (such as Bluetooth™), and another that operates according to a communications technique operating in the implantable medical device (such as Frequency Shift Keying). A software application is installed on the consumer electronics device, which provides a user interface for controlling and reading the implantable medical device. The software application is downloadable from the Internet for example using standard means for interfacing with the consumer electronics device, such as the phone's wireless network. The bridge device, when used in conjunction with the application running on the consumer electronics device, can eliminate the need for a patient to carry a separate external controller otherwise provided by the manufacturer of the implantable medical device. The bridge is preferably small, and easily and discreetly carried by the implantable medical device patient. The bridge is preferably also simple to operate, and may have only a simple user interface, or no user interface at all.

Figure 3:
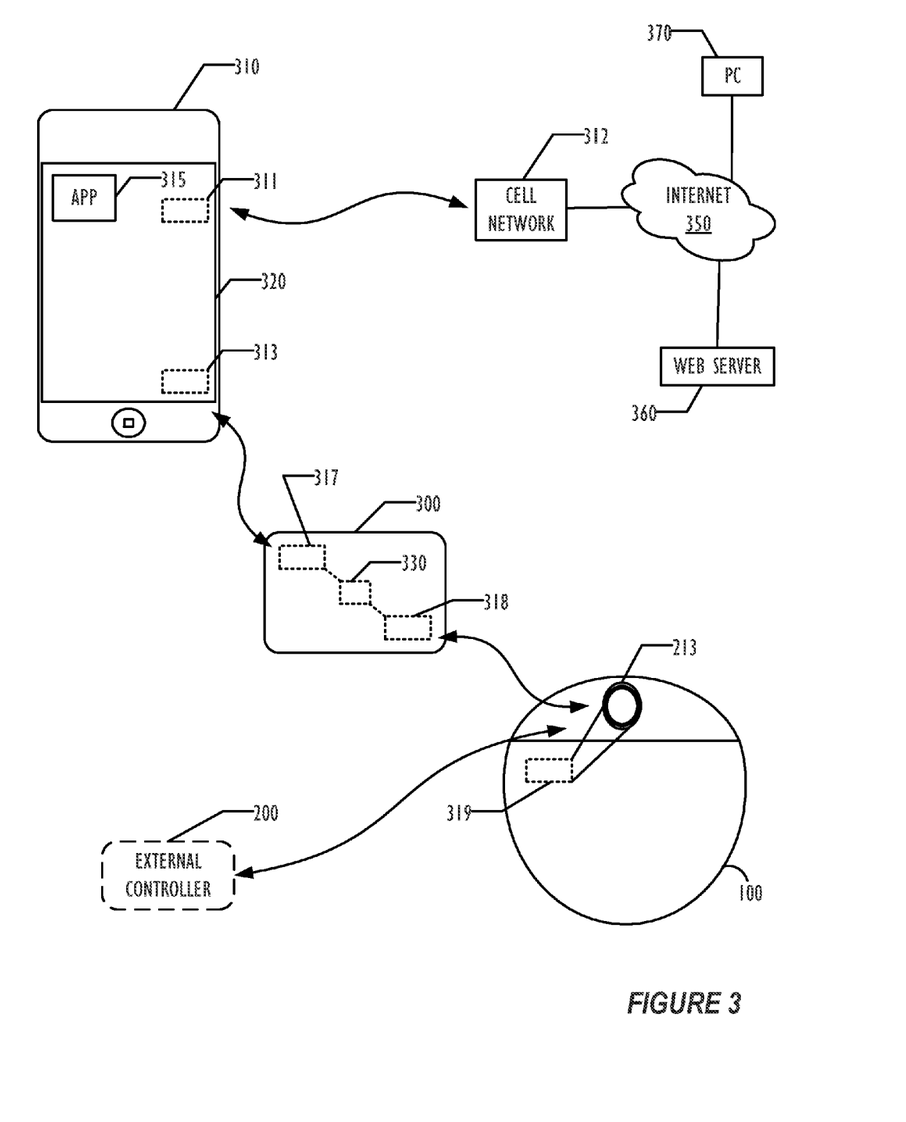
FIG. 3 illustrates a system for communicating between a consumer electronics device and an implantable medical device via a bridge device according to one embodiment.

A communications bridge device 300 as just described, and the system in which it operates, is illustrated in FIG. 3. The bridge 300 is preferably small, and may for example be sized and shaped similar to pagers or insulin pumps. In a preferred embodiment, the bridge 300 is portable for a patient, meaning for example that it is hand-holdable or wearable either on the patient's body or in his/her clothing (e.g., a pocket or backpack). The bridge 300 may be generally rectangular. The bridge 300 may be discreet and not stand out as an obvious medical device. The bridge 300 is typically paired with a specific type of IPG 100, or a particular IPG 100.

Consumer electronics device 310 preferably comprises a smart phone, but can also comprise other communication devices (PDAs, pad, tablet, or notebook computers, etc.). For ease of manipulation, it is preferred that the consumer electronics device 310, like the bridge 300, be portable for a patient. For simplicity, and in recognition of the preferred implementation, the consumer electronics device 310 will be generally referred to in this disclosure as a phone 310. Many patients today carry a phone 310 using a Windows Phone 7®, Android®, or iPhone®-type operating system for example, thus enabling use and dissemination of the disclosed technique.

The phone 310, as is typical, has communication (transceiver) circuitry 311 for voice and data communication with a cellular network 312, and short-range communication (transceiver) circuitry 313 for communicating with other devices at a short distance, such as vehicular telematics systems, other computer devices, etc. The cellular network 312 can in turn be connected to other networks, such as the Internet 350. Transceiver circuitries 311 and 313 in the phone 310 typically operate in accordance with different communication protocols. For example, transceiver 311 may communicate with the cellular network 312 via CDMA, TDMA, or GSM (for voice), or GPRS, GTE, LTE, and WiMAX (for data). Transceiver 313, on the other hand, typically operates using a short-range protocol, such as Bluetooth®, WiFi, or Zigbee® usable with transceiver 311. Because the phone 310 communicates with the bridge 300 using the pre-existing short-range transceiver 313, it requires no special hardware modifications. Each of the transceiver circuits 311 and 313 are coupled to antennas in the phone 310 (not shown).

Custom software application 315 would typically be provided by the manufacturer of the IPG 100 and the bridge 300. As such, the manufacturer may provide or use a web server 360 for providing the application to the Internet 350, where it can be downloaded onto the patient's phone 310 via the cellular network 312. Processes for downloading applications to a communications device such as phone are well known, and require no further explanation. Web server 360 may alternatively take the form of an on-line application store, such as the iTunes® application store managed by Apple Inc. The manufacturer of the IPG 100 and bridge 300 may make the application 315 available only to patients who have purchased a service plan, either as a one-time charge or as a subscription. The manufacturer may also allow third-party developers to develop, modify, or improve the application 315.

Once downloaded, the application 315 may appear as an icon on the display 320 of the phone 310. The patient can then use this icon to access the application 315, and interface with the IPG 100 by way of the bridge as an intermediary. As will be explained in detail later, application 315 will allow the patient to control and monitor operation of his/her IPG 100. When activated, the application 315 will enable or use the short-range transceiver 313 in the phone 310 to communicate with a similar short-range transceiver 317 in the bridge 300. As such, the phone 310 and bridge 300, via control of the software application 315, form a wireless personal area network using Bluetooth™ or other short-ranged communications protocol. As is known, a personal area network is a network for interconnecting devices centered around an individual person's workspace. Although this network is wireless when a Bluetooth™ protocol is used, the connection between the phone 310 and the bridge 300 may also be wired (not shown). Because the phone 310 and bridge 300 are designed to be proximate to the patient, use of such a personal area network is sensible.

The bridge 300 will in turn will repackage the communications received at transceiver 317 to a different communication technique suitable for transmission to the IPG 100. In this regard, communications received from the phone 310 are received at a microcontroller 330 operating in the bridge 300, which microcontroller can comprise any suitable core logic for the device such as a microprocessor, logic circuit, a PLA, whether integrated or not, etc. The microcontroller 330 would usually comprise a single integrated circuit, but this is not necessary, and any logic circuitry capable of performing the functions described herein can be used. "Microcontroller" should be interpreted as consistent with this broad description.

Because the IPG 100 typically already contains transceiver circuitry 319 for wirelessly communicating with other devices (e.g., the external controller 200 of FIG. 2) via an FSK technique as described in the Background, the bridge 300 is also fitted with a FSK-compliant transceiver circuitry 318. (Further details concerning FSK transceiver circuitry useable in an IPG system, and implementable in the bridge 300, can be found in U.S. Patent Publication 2010/0318159, which is incorporated herein by reference). The microcontroller 330 sends the reformatted data to the transceiver circuitry 318, where it is in turn transmitted via FSK to the IPG's telemetry coil 213 and then to transceiver circuitry 319. Communications from the IPG 100 to the phone 310 would occur similarly, with the microcontroller 330 effecting the FSK-to-Bluetooth conversion. Like the phone 310, the IPG 100 requires no special hardware to communicate with the bridge 300, and otherwise communicates with the phone 310 via the bridge 300 just as it would with a traditional external controller 200 (FIG. 2). Note that use of an FSK technique between the bridge 300 and IPG 100 is merely illustrative, and other techniques could be used as well.

As just discussed, the two transceivers 317 and 318 in bridge 300 operate with different communication techniques, one of which (Bluetooth™) is a Radio-Frequency (RF) based protocol, and the other of which (FSK) is based on different physics enabled by magnetic inductive coupling. These different types of techniques are preferred because they match with the techniques traditionally already available in the phone 310 and the IPG 100. However, these techniques are also merely exemplary.

Notice in FIG. 3 that a traditional external controller 200 can still comprise part of the system, i.e., the manufacturer can still design and supply a traditional external controller 200 to control and monitor the IPG 100 in addition to providing the application 315 and bridge 300 useable with a patient's phone 310. However, a patient need not use the external controller 200, or may only use it in an emergency or if the application 315 or bridge 300 fails for some reason. In any event, because a patient will typically often already be carrying a phone 310, the patient need only carry the smaller, simpler bridge 300 instead of the bulkier, more complicated external controller 200 to control and monitor the IPG 100.

The bridge device 300, as enabled by application 315 on the phone 310, is expected to be much simpler and cheaper for an implantable device manufacturer to create compared to a traditional external controller 200 (FIG. 2). In particular, the implant manufacturer need not worry about designing the hardware for the IPG user interface, because the pre-existing user interface of the phone 310 (display, buttons, etc.) is used instead. Moreover, this new approach to interfacing with an IPG 100 may allow the manufacturer to more quickly add additional functionality and features to improve patient experience with his/her IPG 100. Furthermore, because of the native connectivity between the phone 310 and the Internet 350, this new approach should make it easier for the manufacturer to maintain and service the entire IPG system.

Figure 4:
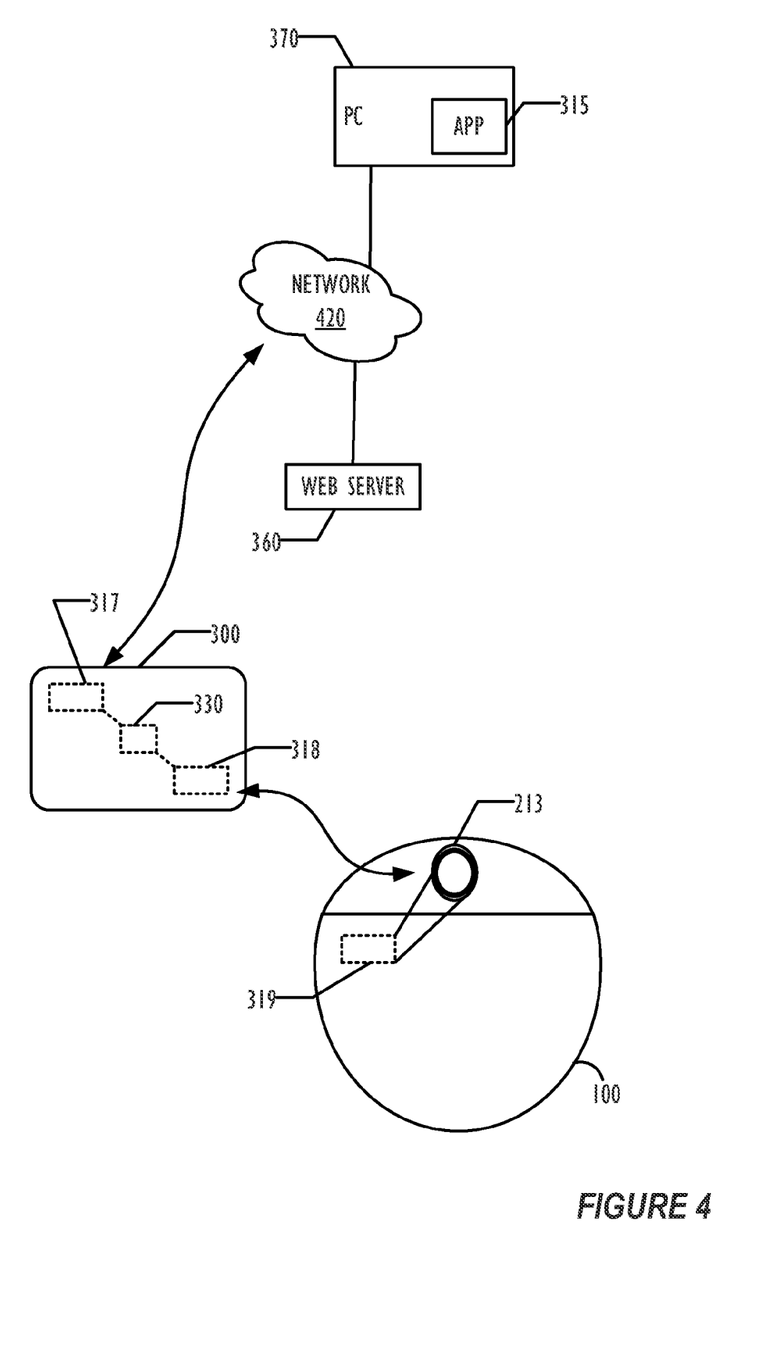
FIG. 4 illustrates a system for communicating between a computer and an implantable medical device via a network and a bridge device according to one embodiment.

The bridge 300 may be used to bridge the IPG 100 to other types of devices, including computers and computer systems. In one embodiment, illustrated in FIG. 4, the bridge 300 may communicate with a personal computer 370 via a network 420, which network may again comprise the Internet. The bridge 300 may be connected to the network 420 using any desired wireless protocol with which its transceiver 317 is complaint, such as any of the long- or short-range protocols already mentioned (e.g., CDMA, TDMA, GSM, GPRS, GTE, LTE, WiMAX, Bluetooth™, WiFi, or Zigbee™). Alternatively, the bridge 300 may be wired to the network 420. Regardless of how the bridge 300 is coupled to the network 420 it can be controlled by a computer 370 coupled to the network 420, which computer 370 runs the software application 315 as already described. In short, using the bridge 300 as an intermediary, the patient may control and monitor operation of his/her IPG 100 using a user interface provided on the computer 370. This user interface is described in further detail below. In yet another embodiment, the bridge 300 may provide a built-in Web server that provides a web interface to allow the bridge 300 to be controlled from any web browser without a unique software application 315 installed on the phone 310 or computer 370. In such an embodiment, the user interface described below may be provided by the Web server on the bridge 300 instead of by the application 315.

Figure 5A:
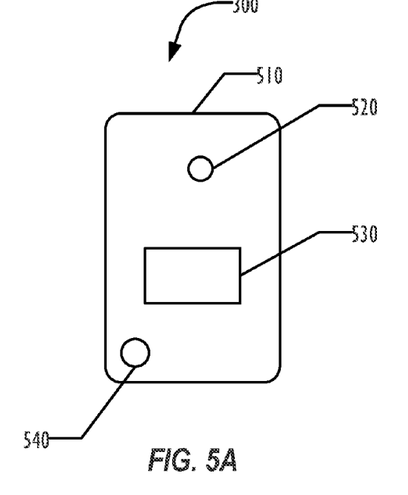
FIG. 5A-5D illustrates features of a bridge device according to one embodiment.

FIG. 5A is a top view of a bridge 300 according to one embodiment. The bridge 300 in this embodiment needs only minimal controls, because the phone 310 and associated application 315 may provide the user interface to control the IPG 100. Thus, in this embodiment, a single switch 530 and a single indicator light 520 may be sufficient. In addition, to allow the bridge 300 to be attached to a keychain, a hole 540 may be provided through a housing 510 of the bridge 300. Other techniques (e.g., hooks, straps, snaps, etc.) may be used to allow attaching the bridge 300 for wear by the patient as desired. Other embodiments may omit attachment mechanisms, allowing the bridge 300 to be carried easily in a pocket, for example. In one embodiment, the switch 530 may turn the bridge 300 on or off, or signal the IPG 100 to turn stimulation on or off, or both. The ability to turn simulation off using the switch 530 is preferred for patient safety in case of IPG 100 malfunction, and is particularly useful in case the phone 310 or application 315 is unable to control the IPG 100 because of their own malfunctions.

For simplicity and robustness in design, the bridge 300 preferably does not contain any ports (e.g., USB, IR ports, power input ports, etc.), as would be common with conventional external controllers 200 (FIG. 2). Instead, it is preferred that the bridge 300 communicate wirelessly with the phone 310 and the IPG 100.

Figure 5B:
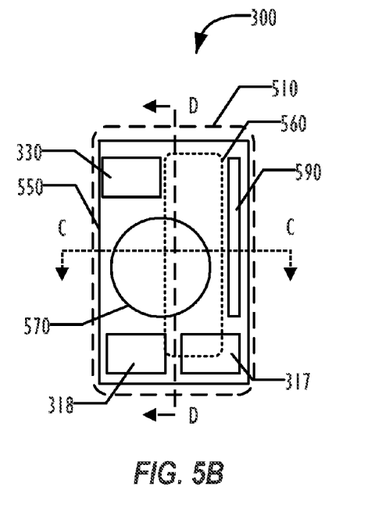
Figure 5C:
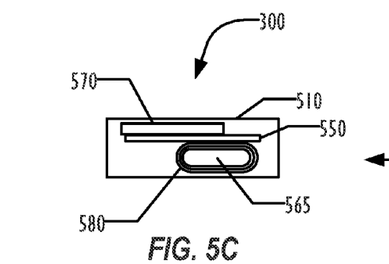
Figure 5D:
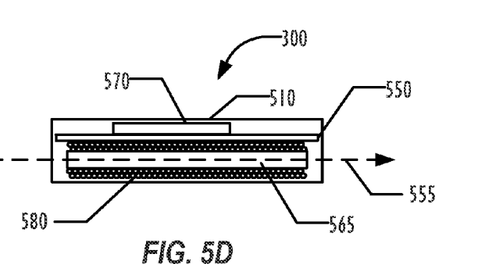

FIG. 5B is a cutaway view of the bridge 300 of FIG. 5A showing its internal components, while FIGS. 5C and 5D provide right angled cross sections. A conventional external controller 200 (FIG. 2) typically uses a flat air core coil antenna. Because of the smaller size of the bridge 300, an air core coil antenna such as the coil 217 of FIG. 2 may have difficulty in achieving a desired telemetry distance with the IPG 100, which should be at least 12 inches and more preferably at least 24 inches. Such ranges allow positioning the bridge 300 in front of the patient, even when the IPG 100 is implanted at the back of the patient.

To achieve this desired communication distance, as illustrated in FIGS. 5B-5D, one embodiment of the bridge 300 uses a ferrite core antenna 560 comprising windings 580 wound around a ferrite core 565 having a long axis 555 (FIG. 5D). The ferrite core antenna 560 is oriented longitudinally with the housing 510. Alternatively, in some embodiments, an air core antenna can be used, winding the antenna windings around the perimeter of the housing 510. Such an antenna would be lighter and possibly more robust than a ferrite core antenna, but could reduce communication distance to the IPG 100. The orientation between the bridge 300 and the IPG 100 will also affect communication distance. See, e.g., U.S. Patent Publication 2009/0069869. However, appropriate design and control of the ferrite core antenna 560 can allow the patient to wear or hold the bridge 300 without orientation concerns.

Also shown in FIGS. 5B-5D are other internal components of the bridge 300, including printed circuit board (PCB) 550, battery 570, microcontroller 330, short-range transceiver circuitry 317, and FSK transceiver circuitry 318. The microcontroller 330, short-range transceiver circuitry 317, and FSK transceiver circuitry 318 are each preferably implemented as their own integrated circuits mounted to the PCB 550, although these can also include numerous discrete components as well. The windings 580 of the ferrite core antenna 560 are soldered to the PCB 550, and are in turn coupled to the short-range FSK transceiver circuitry 318. The short-range transceiver circuitry 317 is coupled to a short-range antenna 590. A short-range antenna 590 operable at Bluetooth frequencies for example can be formed in many different ways as is well known. For example, antenna 590 can comprise a wire monopole, a printed inverted F antenna, a helix, or a surface mount dielectric antenna.

Displays are common in conventional external controllers 200 (FIG. 2), but may be omitted from the bridge 300, reducing its complexity and costs. Instead, the user interface to control and monitor the IPG 100 is provided the phone 310 executing the application 315, as previously noted, and as discussed in further detail later. The phone 310's user interface, via application 315, can also provide status regarding the operation of the bridge 300, such as its battery status.

Only a limited amount of status feedback is available on the bridge 300, which is beneficial to patients desiring the bridge to be simple in construction and operation. For example, a single indicator light 520, typically a light emitting diode (LED), can be used, which may preferably comprise a multi-color LED for enhanced feedback. In one embodiment, the indicator light 520 can indicate multiple statuses. For example, a solid green light for three seconds after a button press can indicates that the IPG 100 successfully received a message from the bridge 300, and that the battery 226 of the IPG 100 (FIG. 2) has an acceptable charge level. If the indicator light 520 is yellow, this can indicate that the message was successfully received, but the IPG 100 battery has an unacceptably low charge level and should be recharged. Recharging the IPG 100 battery 226 is typically not a feature of the bridge 300, and the conventional external controller 200 or an external recharging unit may be used for recharging IPG 100, because the bridge 300 may not provide sufficient energy for a recharging operation. If the bridge 300 failed to communicate with the IPG 100, for example because the bridge 300 was too far away from the IPG 100, then the indicator light 520 can blink yellow, for example, at a 3 Hz rate for 10 seconds. During that time, the bridge 300 automatically and repeatedly retries communication with the IPG 100, which allows the patient to move the bridge 300 closer to or in better alignment with the IPG 100. If successful, then the indicator light 520 can turn to solid green or yellow (depending on the charge level of the IPG 100) for five seconds. These colors, frequencies of blinking, and time periods for the indicator light 520 however are merely illustrative and can be modified, as can the number of indicator lights used. A sound generator (speaker) can also be included in the bridge 300 (not shown), in addition to or in place of the indicator light 520.

Interference between elements of the bridge 300, such as between the electronics on the PCB 550 and the antenna 560, can occur. To reduce such interference, such electronics are preferably positioned off of or away from axis 555 of the antenna 560 as illustrated in FIGS. 5B-5D. In addition, some of the electronics may be shut down or de-powered during bridge communications to reduce interference.

Because of the need for convenience and portability, the bridge 300 is preferably powered by a battery 570, instead of being plugged in to a wall socket. The battery 570 can be a replaceable or rechargeable battery. For example, a replaceable battery 570 can comprise commonly available coin or button-type batteries, such as a CR2025 lithium battery. If a replaceable battery 570 is used, the housing 510 will contain a battery access port (not shown). If a rechargeable battery is used, the housing 510 can be fitted with cradle contacts, a USB port, or any other means generally known for recharging batteries in a portable electronic device. Battery 570 may also be inductively charged upon receipt of a magnetic field at antenna 560 as is well known.

Figure 6:
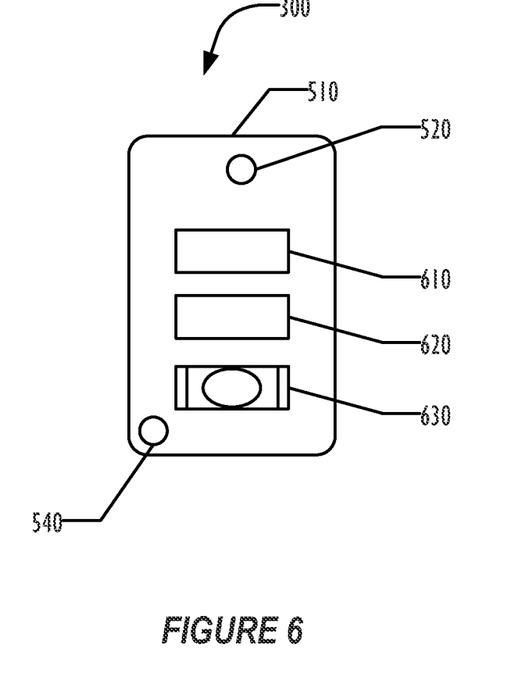
FIG. 6 illustrates features of a bridge device according to another embodiment.

As shown in FIG. 6, the bridge 300 may include limited remote control capability that can perform simple IPG control functions such as increasing or decreasing the amplitude of the simulation by the IPG 100 and turning the simulation on or off. For example, button 610 may increase the amplitude of stimulation, button 620 may decrease the amplitude of simulation, and button 630 may turn stimulation on and off. Button 630 may be recessed to reduce accidental activation of button 630. User interaction elements of the bridge 300 may also be implemented as buttons, slide switches, rocker switches, or any other desired type of mechanism for interacting with the bridge 300. Buttons (or other type of user interaction element) may be at least 19 mm wide to allow a patient with poor eyesight, and flexibility, or hand-eye coordination to press the desired button accurately. In some embodiments, the buttons may be 15 mm tall by 20 mm wide.

Figure 7:
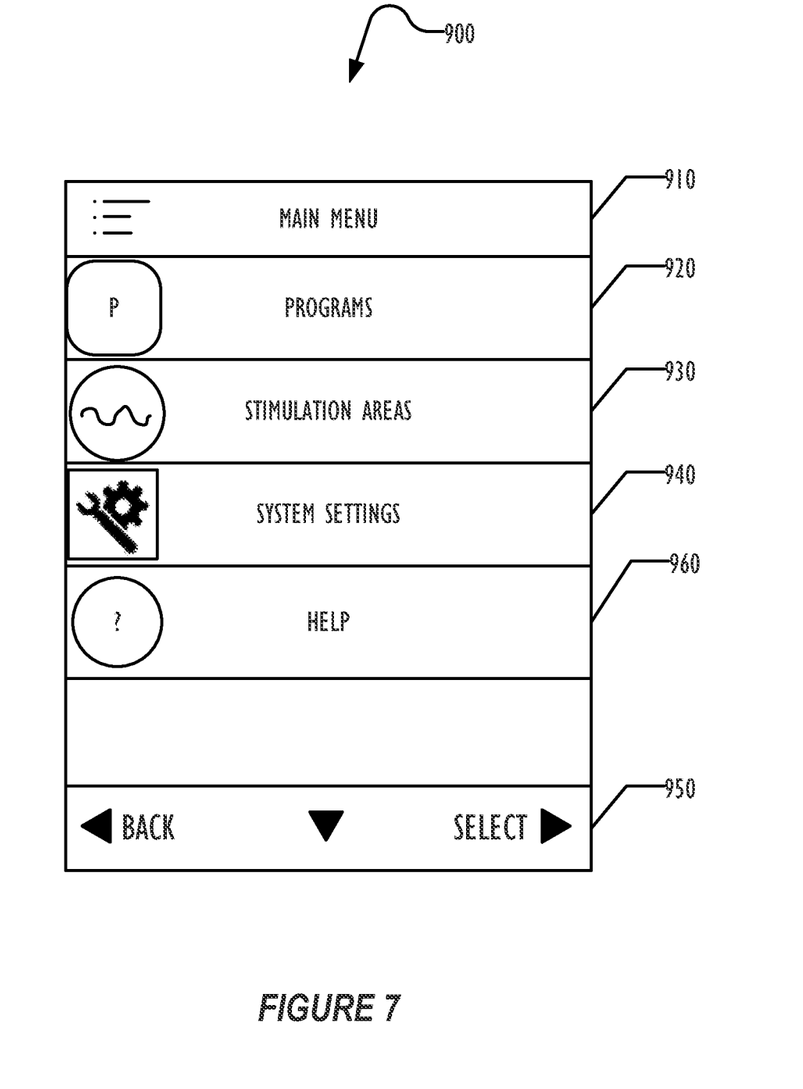
FIGS. 7-9 illustrate portions of a user interface for an application executed on a consumer electronics device according to one embodiment.
Figure 8:
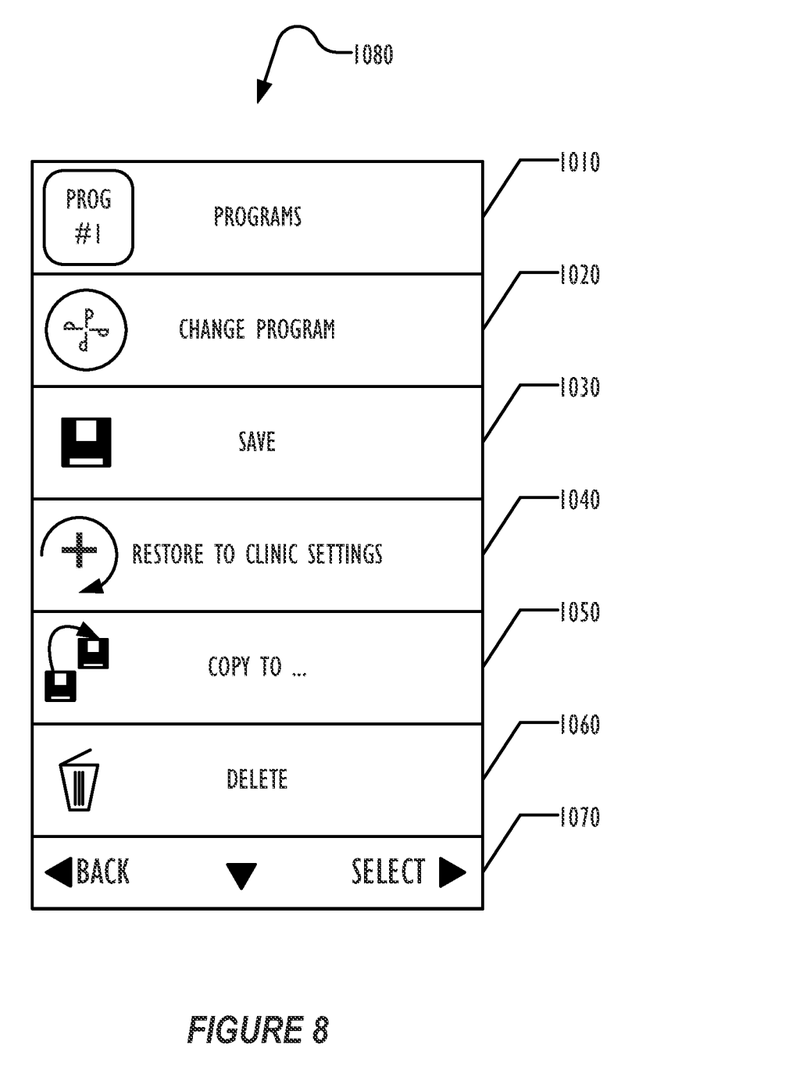
Figure 9:
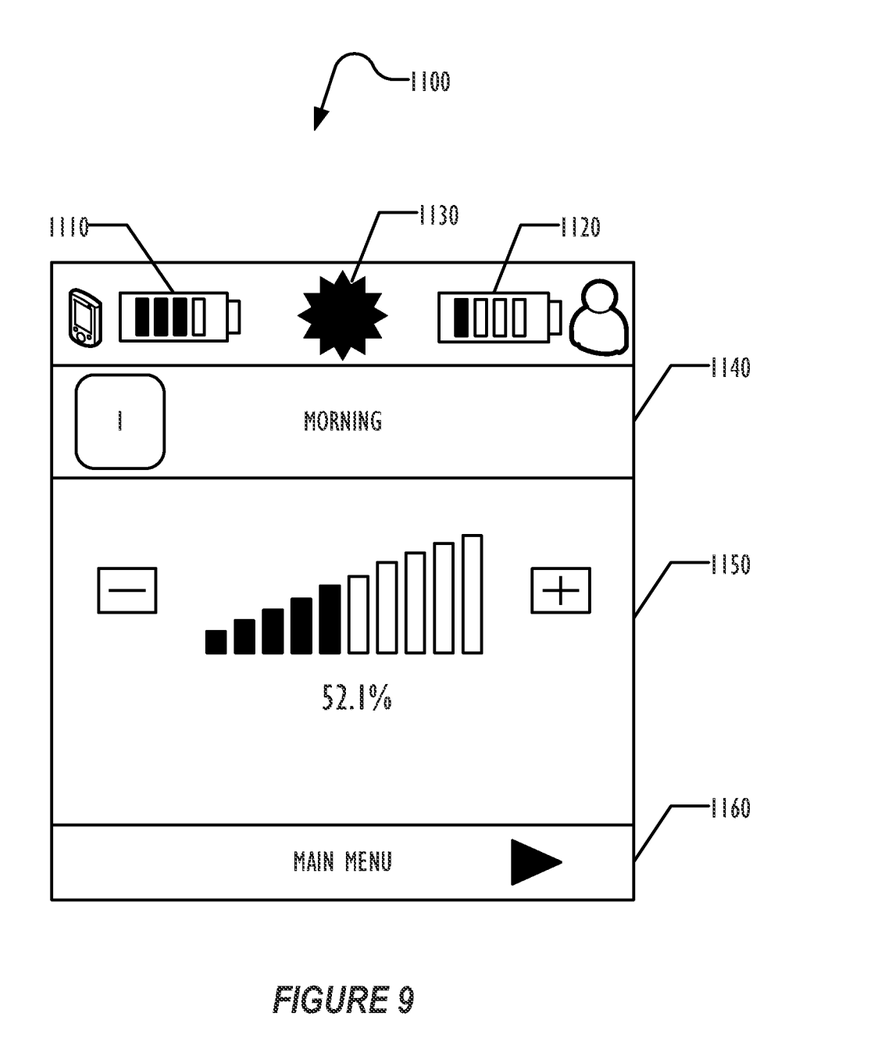

FIGS. 7-9 illustrate some features of the application 315 according to one embodiment, and more specifically provide screen shots taken from the display 320 (FIG. 3) of the phone 310 in which the application 315 is operating. The application 315 may employ any desired programming and user interface techniques to interface with and control the bridge 300, and hence the IPG 100. Because the application 315 on the phone 310 does not depend on the hardware and firmware of the bridge 300 and the IPG 100, the application 315 may be updated or replaced as desired, without requiring access or changes to the bridge 300.

Figures 1A, 1B:
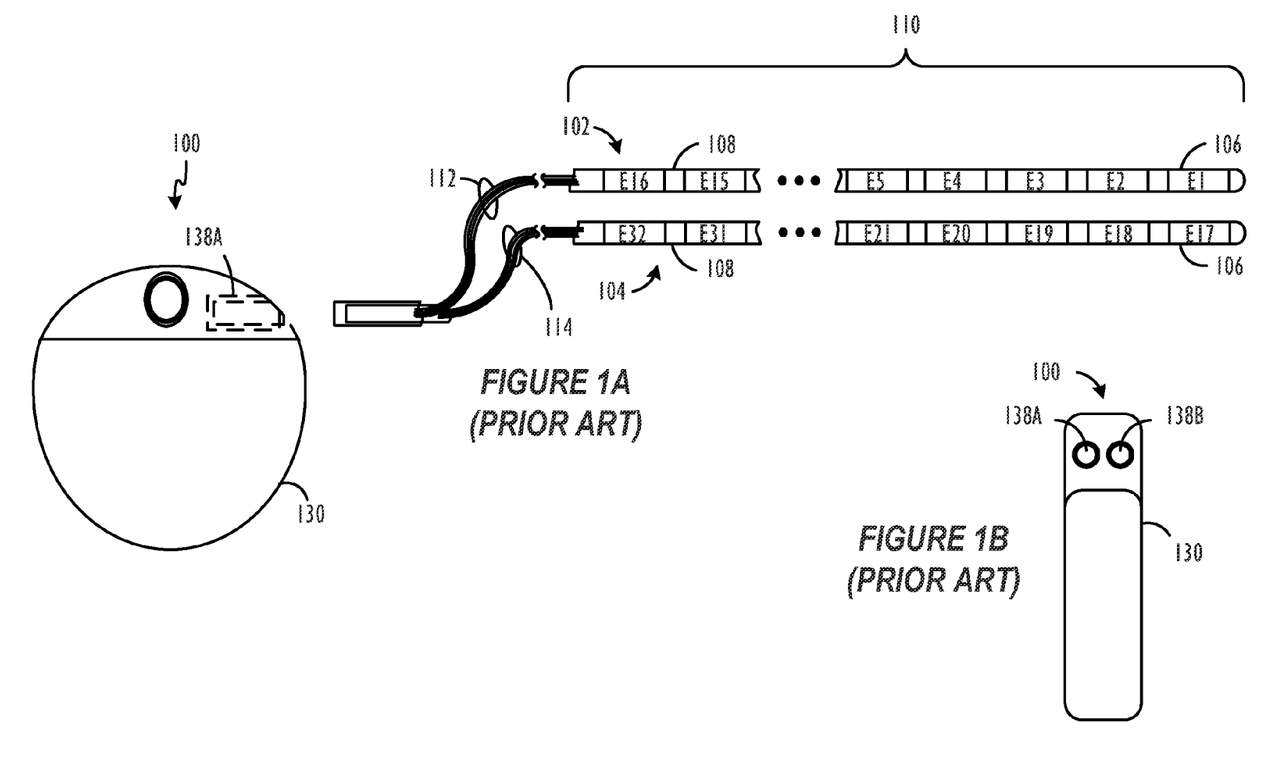
FIG. 1 illustrates conventional implantable medical devices according to the prior art.

As shown in FIG. 7, the main menu 900 provides four features of interest. A menu bar 910 indicates the user's position in the user interface, and currently indicates that the application 315 is displaying the main menu 900. A programs entry 920 allows the patient to select between different stimulation programs to be provided by the IPG 100 to the patient, which programs as noted earlier may be situational and may involve different stimulation parameters. Such stimulation programs would typically be stored in the phone 310 and associated with the application 315. However, the programs may alternatively be stored elsewhere, such as in the bridge 300 itself, and queried by the application 315 in the phone 310. A stimulation areas entry 930 allows the patient to change the areas that are stimulated by the IPG 100. For example, upon selecting 930, the patient may change the electrodes 106 (FIG. 1A) through which stimulation is being delivered. A system settings entry 940 allows the patient to modify settings of the bridge 300. Finally, a selection bar 950 allows the user to navigate the user interface provided by the application 315. A help feature 960 allows the patient to call a customer call center to ask questions or receive assistance, or to access an information website hosted by the manufacturer of the bridge 300 and IPG 100. In some embodiments, the assistance provided may allow the manufacturer to remotely interact with and control the application 315 via the Internet 350 for example, or to collect information from the bridge 300 or IPG 100.

FIG. 8 illustrates a screen 1080 for changing stimulation programs, resulting from the earlier selection of the programs entry 920 (FIG. 7). In this example, area 1010 indicates which program is currently being used by the IPG 100 ("Prog #1"), and when selected allows the patient to change certain stimulation parameters, such as intensity. Area 1020 allows the patient to select a new program. In one embodiment, the patient can cycle through a number of programs for the IPG 100. Upon activating a different program, the application 315 may send instructions to the bridge 300 to reprogram the IPG 100 accordingly. Area 1030 allows the user to save changes that may have been made to the active program. Area 1040 allows the patient to restore the program to the settings that were predefined by the patient's clinician, for example, when the implantable medical device was initially tailored by the clinician for the patient during a fitting procedure. Area 1050 allows the patient to copy one program into another program, allowing the patient to change the copy while leaving the original unchanged. Area 1060 allows the patient to delete a program. Finally, area 1070 allows the patient to navigate the user interface 900.

FIG. 9 illustrates a screen 1100 for allowing the patient to change certain stimulation parameters of the currently active program, resulting from the earlier selection of the programs entry 1010 (FIG. 8). Icon 1110 indicates the battery charge status of the bridge 300, while icon 1120 indicates the battery status of the IPG 100. The user can take appropriate steps (changing the bridge's battery; recharging the IPG battery) in response to these charge statutes. Icon 1130 indicates that stimulation is currently being generated by the IPG 100. Area 1140 indicates the name of the program currently active on the IPG 100. Area 1150 indicates the stimulation strength of the currently active program. In one embodiment, the stimulation strength is shown both in terms of ascending bars as well as by a numerical percentage value. The patient may increase or decrease the stimulation strength using the plus or minus buttons in area 1150 as desired. Finally, area 1160 may be used to navigate the user interface 900.

The user interface 900 illustrated in FIGS. 7-9 is but one example only. Other types of user interface controls for the IPG 100, other indications of IPG and bridge status and feedback, and other arrangements of the user interface, may be used as desired. For example, although screen 1100 illustrates allowing the patient to alter stimulation strength, similar controls could be provided to allow the patient to change other stimulation parameters, including stimulation pulse width and stimulation frequency. Contact information for the patient may be stored or made available through the user interface 900; similarly, contact information for a clinic or for a manufacturer of the bridge 300 may be stored and made available by user interface 900 of the application 315.

Application 315 may also collect data, and as such the system is benefited by the ability to use the phone 310's memory, which is generally ample. For example, various IPG and control and monitoring data can be transferred and stored at the phone 310, such as the number of times a stimulation program is changed, whether the stimulation of the IPG 100 is turned on or off, etc. The application 315 may also store other data regarding the use of the application 315, the bridge 300, or the IPG 100. The collected data may then reviewed by the patient, clinician, or manufacturer using the application 315, or can be transmitted from the phone 310 via the Internet 350 for review by these entities as desired. The application 315 may periodically transmit such data in real-time, at time intervals, or upon synchronizing with another consumer electronics device. For this purpose, the bridge 300 in some embodiments may have a full-time network connection for updating, monitoring, etc.

The bridge 300 itself may also similarly act as a data-gathering device, although this may require the provision of additional memory in the bridge 300. The bridge 300 may communicate with the phone 310 at a faster transmission rate than the transmission rate between the bridge 300 and the IPG 100. As such, the bridge 300 may collect data from the IPG 100, store the collected data on the bridge 300, and then transfer the stored data to the consumer electronics device 310 at a later time.

Because techniques for programming applications on the phone 310 are well known, development of the application 315 may be easier than the development of firmware for a conventional customized external controller 200. As such, the manufacturer of the IPG 100 and the bridge 300 can more quickly and easily develop improved IPG 100 control and monitoring features, reducing or eliminating the costs associated with developing, manufacturing, and supporting a custom traditional external controller 200 (FIG. 2). In addition, the manufacturer can deploy software updates to both the bridge 300 and the IPG 100 using the disclosed system. For example, the manufacturer's web server 360 (FIG. 3) can be provided with operating software updates for the microcontrollers in either of these devices. When the patient's phone is connected to this server, such updates can be downloaded to the phone 310, and then to the bridge 300 and/or the IPG 100 through the communication links previous described. Alternatively, the application 315 may provide the user the option to make software updates to these devices once such updates have been received at the phone 310. If the bridge 300 contains a web server, as discussed earlier with respect to FIG. 4, then such updating may take place without using the phone 310 as an intermediary. Updating the software via the disclosed system reduces or eliminates the need for the patient to visit a clinician's office to receive such software updates, as is typically required with conventional external controllers 200.

The bridge 300 can also managing multiple of a patient's implanted devices, e.g., multiple IPGs 100 as might typically be used in a deep brain stimulator (DBS) network for example.

Other functionality and features may be included in the bridge 300. For example, in one embodiment, the bridge 300 may function as an external trial stimulator (ETS) which is controlled by the software application 315 on the phone 310. See, e.g., U.S. patent Publication 2010/0228324 (discussing ETS technology).

Figure 10:
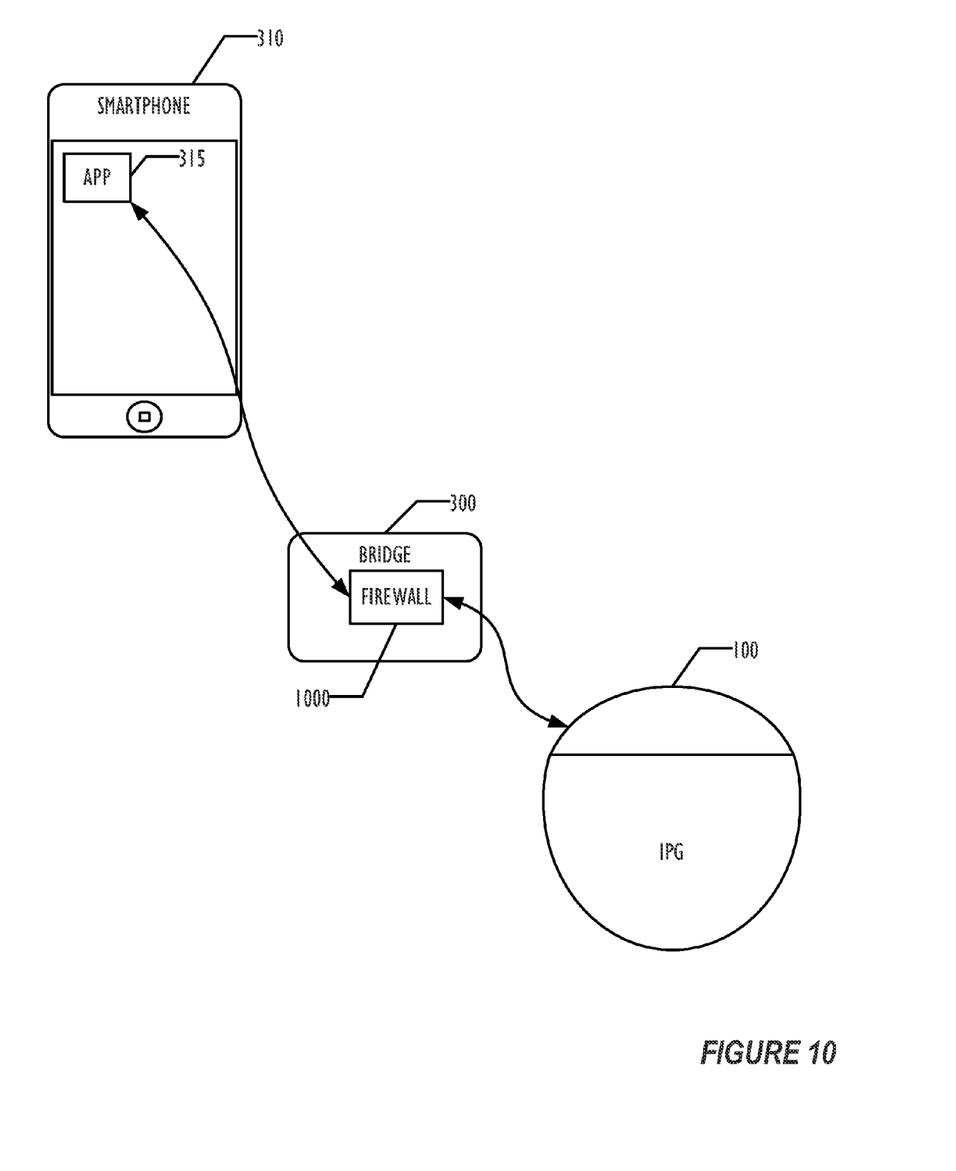
FIG. 10 illustrates features of a bridge device including a firewall according to one embodiment.

In one embodiment, the bridge 300 may contain a firewall component 1000, as illustrated in FIG. 10, to control communications between the application 315 on the smartphone 310 and the IPG 100. The firewall component 1000 may be implemented in the hardware of the bridge 300, software that executes on the microprocessor 330, or a combination of both. The firewall 1000 provides a secure and robust control functionality for the bridge 300.

The firewall component 1000 may filter packets received by the bridge 300 from the smartphone 310, to protect the IPG 100 from unauthorized access, whether malicious or accidental, while permitting legitimate communications to pass. The firewall component 1000 may, for example, allow communications only from registered or paired smartphones 310, to prevent malicious or accidental attempts to communicate with the IPG 100 by unauthorized devices. Typically, the firewall 1000 runs configuration rules that define which communications to accept and which to reject.

The firewall component may be a simple packet filter, inspecting each packet of data received via the transceiver 317 and rejecting packets received from any device other than the currently registered smartphone 310. The rules describing packet filtering may also ensure that only packets received on a predetermined port or ports are accepted.

The firewall 1000 may also employ stateful filtering techniques that examine each packet in the context of the communication session between the smartphone 310 and the bridge 300. To achieve stateful filtering, the firewall 1000 may record information about a connection state between the smartphone 310 and the bridge 300.

In addition, the firewall 1000 may provide application layer protection techniques, examining the commands received from the smartphone 310, in addition to packet layer validation as describe above. Each command received from the smartphone 310 may be validated to ensure that the command is a valid command and would not put the IPG 100 into an unsafe condition if executed by the IPG 100. Commands that would put the IPG 100 into an unsafe condition may be rejected or possibly modified to avoid the unsafe condition.

Although described above as being implemented in the bridge 300, in one embodiment, the firewall 1000 may be implemented at least in part in the smartphone 310, or may be implemented partly in the smartphone 310 and partly in the bridge 300. If implemented in the smartphone 310, the firewall 1000 is preferably implemented as an interface to the smartphone 310's hardware communication physical layer, to ensure that the firewall 1000 can intercept and analyze all communications between the application 315 and the bridge 300. In such an embodiment, however, a portion of the firewall component 1000 may be implemented in the bridge device to provide the protection against unauthorized or malicious communications, while the portion of the firewall 1000 implemented in the smartphone 310 provides the protection against improper or dangerous commands generated by the application 315, or any other application on the smartphone 310 that might inadvertently or maliciously attempt to communicate with the IPG 100.

The firewall component 1000 is not limited to embodiments implementing a bridge 300, but may be implemented in embodiments in which the device 310 communicates directly with the IPG 100, preferably as an interface to the device 310's hardware communication physical layer, for the reasons described above.

It is to be understood that the above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

What is claimed is:

1. A communication bridge device for communicating with an implantable medical device and a consumer electronics device, comprising:
a housing, wherein the housing is portable for a patient;
first transceiver circuitry coupled to a first antenna in the housing configured for wirelessly receiving communications from the consumer electronics device in accordance with a first communications technique;
second transceiver circuitry coupled to a second antenna in the housing configured for wirelessly communicating with the implantable medical device in accordance with a second communication technique; and
a microcontroller in the housing coupled between the first transceiver circuitry and the second transceiver circuitry,
wherein the microcontroller is programmed to relay the received communications to the implantable medical device via the second transceiver circuitry to allow the consumer electronics device to control the implantable medical device, and
wherein the microcontroller is further programmed to provide a firewall between the consumer electronics device and the implantable medical device, the firewall configured to perform one or more of the following:
an examination of the communications in accordance with a connection state between the consumer electronics device and the communication bridge device,
an examination of the communications to determine if commands in the communications would put the implantable medical device in an unsafe condition if executed by the implantable medical device.

2. The device of claim 1, wherein the second communication technique is implemented using a magnetic inductive coupling.

3. The device of claim 1, wherein the second communication technique comprises Frequency Shift Keying.

4. The device of claim 1, wherein the first communication technique comprises a short-range RF protocol.

5. The device of claim 1, wherein the first communication technique establishes a personal area network.

6. The device of claim 1, wherein the first antenna comprises an RF antenna, and wherein the second antenna comprises a coil antenna.

7. The device of claim 6, wherein the RF antenna comprises a wire monopole, a printed inverted F antenna, a helix, or a surface mount dielectric antenna.

8. The device of claim 6, wherein the coil antenna is wrapped around a ferromagnetic core.

9. The device of claim 6, wherein the coil antenna is wrapped around an axis parallel to a long axis of the housing.

10. The device of claim 1, wherein the housing comprises no user interface.

11. The device of claim 1, wherein the housing is additionally configured to operate as a key chain.

12. The device of claim 1, wherein the housing comprises an on/off switch, and no other input means.

13. The device of claim 1, wherein the housing comprises an indicator light, and no other indicator means.

14. The device of claim 1, wherein the housing comprises buttons for increasing and decreasing stimulation.

15. The device of claim 1, wherein the firewall rejects the communications from unregistered consumer electronics devices.

16. The device of claim 1, wherein the firewall only relays the communications when the consumer electronics device is paired with the bridge.

17. A system, comprising:
an implantable medical device configured to provide therapy to a patient;
a software application configured for execution by a consumer electronics device with a user interface that is portable for a patient, wherein the software application configures the user interface of the consumer electronics device to allow a user to send communications to the bridge to control the therapy provided by the implantable medical device via the bridge; and
a portable bridge for relaying the communications to the implantable medical device from the consumer electronics device, the bridge comprising a housing containing:
first transceiver circuitry coupled to a first antenna configured to wirelessly receive the communications from the consumer electronics device,
second transceiver circuitry coupled to a second antenna configured to wirelessly transmit the communications to the implantable medical device, and
control circuitry comprising a firewall between the first transceiver circuitry and the second transceiver circuitry, wherein the firewall is configured to perform one or more of the following:

an examination of the communications in accordance with a connection state between the consumer electronics device and the bridge, an examination of the communications to determine if commands in the communications would put the implantable medical device in an unsafe condition if executed by the implantable medical device.

18. The system of claim 17, further comprising an external controller with a user interface, wherein the user interface is used to wirelessly control and monitor the implantable medical device.

19. The system of claim 17, wherein the consumer electronics device comprises a mobile phone.

20. The system of claim 17, wherein the consumer electronic device is configured to communicate with a voice and data with a network.

21. The system of claim 20, wherein the network comprises a cellular network.

22. The system of claim 20, wherein the network comprises the Internet.

23. The system of claim 20, wherein the consumer electronic device operates pursuant to a protocol to communicate with the bridge, and can communicate using the protocol with additional devices in addition to the bridge.

24. The system of claim 20, wherein the software application is downloadable to the consumer electronics device via the network.

25. The system of claim 17, wherein the software application is further configured to connect via a network to an information source provided by a manufacturer of the implantable medical device.

26. The system of claim 25, wherein the information source comprises a call center.

27. The system of claim 25, wherein the information source comprises a webpage.

28. The system of claim 17, wherein the first transceiver circuitry operates in accordance with a first communication technique, and the second transceiver circuitry operates in accordance with a second communication technique.

29. The system of claim 28, wherein the first communication technique comprises a short-range RF protocol, and wherein the second communication technique comprises Frequency Shift Keying.

30. The system of claim 17, wherein the software application provides options to the user interface to allow the patient to alter a strength of electrical stimulation provided by the implantable medical device.

31. The system of claim 17, wherein the software application provides options to the user interface to allow the patient to turn on or turn off electrical stimulation provided by the implantable medical device.

32. The system of claim 17, wherein the software application provides options to the user interface to allow the patient to alter stimulation parameters of electrical stimulation provided by the implantable medical device.

33. The system of claim 17, wherein the communications from unregistered consumer electronics devices are rejected by the firewall.

34. The system of claim 17, wherein the firewall only relays the communications when the consumer electronics device is paired with the bridge.

* * * * *